(12) United States Patent
Garamszegi et al.

(10) Patent No.: US 8,273,112 B2
(45) Date of Patent: Sep. 25, 2012

(54) PEDICLE SCREW ASSEMBLY

(75) Inventors: Laszlo Garamszegi, Mission Viejo, CA (US); John Carlisle Brown, Balboa, CA (US); Souhail Toubia, San Juan Capistrano, CA (US)

(73) Assignee: Phygen, LLC, Irvine, CA (US)

( * ) Notice: Subject to any disclaimer, the term of this patent is extended or adjusted under 35 U.S.C. 154(b) by 0 days.

(21) Appl. No.: 12/725,401

(22) Filed: Mar. 16, 2010

(65) Prior Publication Data
US 2010/0292740 A1 Nov. 18, 2010

Related U.S. Application Data

(63) Continuation of application No. 11/109,124, filed on Apr. 18, 2005, now Pat. No. 7,678,139.

(60) Provisional application No. 60/563,594, filed on Apr. 20, 2004, provisional application No. 60/598,676, filed on Aug. 3, 2004, provisional application No. 60/612,885, filed on Sep. 24, 2004.

(51) Int. Cl.
*A61B 17/86* (2006.01)

(52) U.S. Cl. ........ 606/306; 606/266; 606/267; 606/270; 606/305; 606/328

(58) Field of Classification Search .......... 606/266–268, 606/270, 301, 305–306, 328
See application file for complete search history.

(56) References Cited

U.S. PATENT DOCUMENTS

| | | | |
|---|---|---|---|
| 1,346,867 | A | 7/1920 | Weibull |
| 2,355,899 | A | 8/1944 | Beede |
| 4,805,602 | A | 2/1989 | Puno et al. |
| 4,887,596 | A | 12/1989 | Sherman |
| 4,946,458 | A | 8/1990 | Harms et al. |
| 4,950,269 | A | 8/1990 | Gaines, Jr. |
| 5,042,982 | A | 8/1991 | Harms et al. |

(Continued)

FOREIGN PATENT DOCUMENTS
DE 19542116 5/1997
(Continued)

OTHER PUBLICATIONS

Derwent Abstract, Accession No. 13941355 for FR 2802796, published Jun. 29, 2001, entitled "Bolt for Connecting Vertebra to Longitudinal Member, e.g. Spine," (iten DY).
Derwent Abstract, Acession No. 9770358 for EP 582857, published Feb. 16, 1994, entitled: "Spinal Column Fixation Component Esp Pedicle Screw or Hook—Comprises Strap Being in Form of Closed Hoop With Moves Only in One Direction as Loop Becomes Smaller, Using Closure Part, and Being Accommadted in Slot Openings in Head Part," (item DW).

(Continued)

*Primary Examiner* — Eduardo C Robert
*Assistant Examiner* — Julianna N Harvey
(74) *Attorney, Agent, or Firm* — Fred C. Hernandez; Mintz, Levin, Cohn, Ferris, Glovsky and Popeo, P.C.

(57) ABSTRACT

Disclosed are spinal fusion assemblies for use in skeletal systems. The assembly includes a coupling element that can be coupled to a fixation element, such as, for example, a screw with a head that removably mates with the coupling element. The coupling element and fixation element are configured to be coupled to an elongate stabilizer, such as a rod, that is positioned between a top and a bottom saddle. A compression member, such as a compression nut, is configured to mate with the coupling element and provides a compressive force to the top and bottom saddles to secure the elongate stabilizer therebetween. The top and bottom saddles are movably positioned within the coupling element such that they can gradually reposition and self-align into a secure engagement with the stabilizer as the compression member provides the compressive force.

10 Claims, 8 Drawing Sheets

U.S. PATENT DOCUMENTS

| | | | |
|---|---|---|---|
| 5,084,048 A | 1/1992 | Jacob et al. |
| 5,092,867 A | 3/1992 | Harms et al. |
| 5,129,388 A | 7/1992 | Vignaud et al. |
| 5,190,543 A | 3/1993 | Schlapfer |
| 5,196,013 A | 3/1993 | Harms et al. |
| 5,207,678 A | 5/1993 | Harms et al. |
| 5,217,497 A | 6/1993 | Mehdian |
| 5,254,118 A | 10/1993 | Mirkovic |
| 5,261,912 A | 11/1993 | Frigg |
| 5,360,431 A | 11/1994 | Puno et al. |
| 5,437,671 A | 8/1995 | Lozier et al. |
| 5,443,467 A | 8/1995 | Biedermann et al. |
| 5,466,237 A | 11/1995 | Byrd, III et al. |
| 5,474,555 A | 12/1995 | Puno et al. |
| 5,476,464 A | 12/1995 | Metz-Stavenhagen et al. |
| 5,496,321 A | 3/1996 | Puno et al. |
| 5,520,689 A | 5/1996 | Schlapfer |
| 5,520,690 A | 5/1996 | Errico et al. |
| 5,534,001 A | 7/1996 | Schlapfer et al. |
| 5,545,165 A | 8/1996 | Biedermann et al. |
| 5,545,166 A | 8/1996 | Howland |
| 5,549,608 A | 8/1996 | Errico et al. |
| 5,554,157 A | 9/1996 | Errico et al. |
| 5,562,688 A | 10/1996 | Riza |
| 5,586,984 A | 12/1996 | Errico et al. |
| 5,593,407 A | 1/1997 | Reis |
| 5,628,740 A | 5/1997 | Mullane |
| 5,647,873 A | 7/1997 | Errico et al. |
| 5,649,926 A | 7/1997 | Howland |
| 5,669,911 A | 9/1997 | Errico et al. |
| 5,672,176 A | 9/1997 | Biedermann et al. |
| 5,683,390 A | 11/1997 | Metz-Stavenhagen et al. |
| 5,690,630 A | 11/1997 | Errico et al. |
| 5,697,929 A | 12/1997 | Mellinger |
| 5,716,356 A | 2/1998 | Biedermann et al. |
| 5,725,527 A | 3/1998 | Biedermann et al. |
| 5,728,098 A | 3/1998 | Sherman et al. |
| 5,733,285 A | 3/1998 | Errico et al. |
| 5,733,286 A | 3/1998 | Errico et al. |
| 5,752,957 A | 5/1998 | Ralph et al. |
| 5,782,833 A * | 7/1998 | Haider .......................... 606/266 |
| 5,797,911 A | 8/1998 | Sherman et al. |
| 5,863,293 A | 1/1999 | Richelsoph |
| 5,879,350 A | 3/1999 | Sherman et al. |
| 5,882,350 A | 3/1999 | Ralph et al. |
| 5,885,286 A | 3/1999 | Sherman et al. |
| 5,891,145 A | 4/1999 | Morrison et al. |
| 5,954,725 A | 9/1999 | Sherman et al. |
| 5,961,517 A | 10/1999 | Biedermann et al. |
| 5,964,760 A | 10/1999 | Richelsoph |
| 5,980,521 A | 11/1999 | Montague et al. |
| 5,989,254 A | 11/1999 | Katz |
| 6,001,098 A | 12/1999 | Metz-Stavenhagen et al. |
| 6,015,409 A | 1/2000 | Jackson |
| 6,022,350 A | 2/2000 | Ganem |
| 6,050,997 A | 4/2000 | Mullane |
| 6,053,917 A | 4/2000 | Sherman et al. |
| 6,063,090 A | 5/2000 | Schlapfer |
| 6,074,391 A | 6/2000 | Metz-Stavenhagen et al. |
| 6,077,262 A | 6/2000 | Schlapfer et al. |
| 6,090,110 A | 7/2000 | MetzStavenhagen |
| 6,090,111 A | 7/2000 | Nichols |
| 6,106,526 A | 8/2000 | Harms et al. |
| 6,113,601 A | 9/2000 | Tatar |
| 6,132,432 A | 10/2000 | Richelsoph |
| 6,132,434 A | 10/2000 | Sherman et al. |
| 6,179,841 B1 | 1/2001 | Jackson |
| 6,183,472 B1 | 2/2001 | Lutz |
| 6,214,006 B1 | 4/2001 | Metz-Stavenhagen |
| 6,248,105 B1 | 6/2001 | Schlapfer et al. |
| 6,261,287 B1 | 7/2001 | Metz-Stavenhagen |
| 6,280,442 B1 | 8/2001 | Barker et al. |
| 6,287,311 B1 | 9/2001 | Sherman et al. |
| 6,296,642 B1 | 10/2001 | Morrison et al. |
| 6,325,802 B1 | 12/2001 | Frigg |
| 6,371,957 B1 | 4/2002 | Amrein et al. |
| 6,443,953 B1 | 9/2002 | Perra et al. |
| 6,454,773 B1 | 9/2002 | Sherman et al. |
| 6,471,705 B1 | 10/2002 | Biedermann et al. |
| 6,485,491 B1 | 11/2002 | Farris et al. |
| 6,488,681 B2 | 12/2002 | Martin et al. |
| 6,537,276 B2 | 3/2003 | Metz-Stavenhagen |
| 6,554,834 B1 | 4/2003 | Crozet et al. |
| 6,565,565 B1 * | 5/2003 | Yuan et al. ................... 606/272 |
| 6,582,436 B2 | 6/2003 | Schlapfer et al. |
| 6,585,737 B1 | 7/2003 | Baccelli et al. |
| 6,610,063 B2 | 8/2003 | Kumar et al. |
| 6,641,586 B2 | 11/2003 | Varieur |
| 6,660,004 B2 | 12/2003 | Barker |
| 6,663,635 B2 | 12/2003 | Frigg et al. |
| 6,695,843 B2 | 2/2004 | Biedermann et al. |
| 6,723,100 B2 | 4/2004 | Biedermann et al. |
| 6,736,820 B2 | 5/2004 | Biedermann et al. |
| 6,755,829 B1 | 6/2004 | Bono et al. |
| 6,770,075 B2 | 8/2004 | Howland |
| 6,783,527 B2 | 8/2004 | Drewry et al. |
| 6,802,844 B2 | 10/2004 | Ferree |
| 6,835,196 B2 | 12/2004 | Biedermann et al. |
| 6,837,889 B2 | 1/2005 | Shluzas |
| 6,843,791 B2 | 1/2005 | Serhan |
| 6,858,030 B2 | 2/2005 | Martin et al. |
| 6,869,433 B2 | 3/2005 | Glascott |
| 7,018,378 B2 | 3/2006 | Biedermann et al. |
| 7,066,937 B2 | 6/2006 | Shiuzas |
| 7,087,057 B2 | 8/2006 | Konieczynski |
| 7,144,396 B2 | 12/2006 | Shluzas |
| 7,211,086 B2 | 5/2007 | Biedermann et al. |
| 2001/0034522 A1 | 10/2001 | Frigg |
| 2001/0056283 A1 | 12/2001 | Carter et al. |
| 2002/0082601 A1 | 6/2002 | Toyama et al. |
| 2002/0120272 A1 | 8/2002 | Yuan et al. |
| 2002/0143341 A1 | 10/2002 | Biedermann et al. |
| 2002/0169450 A1 | 11/2002 | Lange |
| 2002/0183748 A1 | 12/2002 | Martin et al. |
| 2003/0023240 A1 | 1/2003 | Amrein et al. |
| 2003/0055426 A1 | 3/2003 | Carbone et al. |
| 2003/0088248 A1 | 5/2003 | Reed |
| 2003/0100897 A1 | 5/2003 | Metz-Stavenhagen |
| 2003/0100904 A1 | 5/2003 | Biedermann |
| 2003/0125742 A1 | 7/2003 | Yuan et al. |
| 2003/0167058 A1 * | 9/2003 | Shluzas .......................... 606/61 |
| 2004/0039386 A1 | 2/2004 | Kumar et al. |
| 2004/0087978 A1 | 5/2004 | Velez |
| 2004/0181224 A1 | 9/2004 | Biedermann et al. |
| 2004/0186473 A1 | 9/2004 | Cournoyer et al. |
| 2004/0243126 A1 | 12/2004 | Carbone et al. |
| 2004/0260283 A1 | 12/2004 | Wu et al. |
| 2005/0033436 A1 | 2/2005 | Schlapfer et al. |
| 2005/0080419 A1 | 4/2005 | Donath |
| 2005/0154391 A1 | 7/2005 | Doherty et al. |
| 2005/0240180 A1 | 10/2005 | Vinney |

FOREIGN PATENT DOCUMENTS

| | | |
|---|---|---|
| EP | 0608623 | 12/1993 |
| EP | 0582857 | 2/1994 |
| FR | 2802796 | 6/2001 |
| WO | WO 98/34554 | 8/1998 |
| WO | WO 01/08574 | 2/2001 |
| WO | WO 01/47425 | 7/2001 |
| WO | WO 03/024343 | 3/2003 |
| WO | WO 2004/089245 | 10/2004 |

OTHER PUBLICATIONS

Derwent Abstract, Accession No. 11295385 for DE 19542116, published May 15, 1997, entitled: "Device for Fixing Implant to Bone—Has Screw With Rounded Underside of Head Seating in Rounded Seat of Lower Part With Screw Held in Lower Part by Top Insert to Lower Part," (item DV).

US 5,873,378, 2/1999, Harms et al. (withdrawn).

* cited by examiner

PEDICLE SCREW ASSEMBLY

This application is a continuation of U.S. patent application Ser. No. 11/109,124, filed Apr. 18, 2005, entitled, "Pedicle Screw Assembly," which claims priority benefit from U.S. Provisional Patent Application No. 60/563,594, filed Apr. 20, 2004, entitled "Pedicle Screw Assembly"; U.S. Provisional Patent Application No. 60/598,676, filed Aug. 3, 2004, entitled "Pedicle Screw Assembly"; U.S. Provisional Patent Application No. 60/612,885, filed Sep. 24, 2004, entitled "Pedicle Screw Assembly"; each of the above are hereby incorporated in their entireties herein.

BACKGROUND

This disclosure is directed at skeletal bone fixation systems, and more particularly to a fixation assembly for vertebrae of a spinal column.

Spinal fixation systems are used to secure sections of the spinal column, such as vertebral bodies, into a fixed position to correct spinal injuries and defects. Internal fixation is used most frequently in the spine in conjunction with vertebral fusion, and also for the manipulation of the spine to correct spinal deformities. A typical spinal fixation assembly includes a fixation device, such as a screw or hook, that can be attached to a portion of a first vertebral body. The screw can be coupled to a stabilization member, such as an elongate rod, that can be linked to one or more additional vertebral bodies using additional screws.

Pursuant to a general process, two or more bone screws and/or hooks are secured to a vertebral body that is to be stabilized. After the screws are secured to the vertebral bodies, the screws are coupled to a spinal stabilization rod that restricts movement of the stabilized vertebra. It is important that the screws have a secure coupling with the spinal stabilization rod in order to prevent movement of the rod relative to the screw after placement.

It can be a tedious process to position the screws on the vertebral bodies and to interconnect them with the stabilizing rod. Thus, it is desirable that the screws be easily attached to the rods and that, once attached, the coupling between the screw and rod be secure. In view of the foregoing, there is a need for improved bone stabilization systems.

SUMMARY

Disclosed are spinal fusion assemblies for use in skeletal systems. The assemblies may be used in any skeletal region, although they are well adapted for the fixation and manipulation of the spine. In a poly-axial embodiment, the system includes a tulip-like coupling element that can be coupled to a fixation element, such as, for example, a screw with a head that removably mates with the coupling element. The coupling element and fixation element are configured to be coupled to an elongate stabilizer, such as a rod, that is positioned between a top and a bottom saddle. A compression member, such as a compression nut, is configured to mate with the coupling element and provides a compressive force to the top and bottom saddles to secure the elongate stabilizer therebetween. The top and bottom saddles are movably positioned within the coupling element such that they can gradually reposition and self-align into a secure engagement with the stabilizer as the compression member provides the compressive force.

In one aspect, there is disclosed a bone stabilizer assembly, comprising a fixation element adapted to engage a bone and having a head portion and shank portion; a coupling element having an internal bore sized to receive the shank portion of the fixation element and a seat adapted to support the head portion of the fixation element, the coupling element further adapted to receive a stabilizer rod; a bottom saddle movably mounted in the coupling element below the stabilizer rod when the stabilizer rod is in the coupling element; a top saddle positioned above the stabilizer rod when the stabilizer rod is in the coupling element; and a compression nut engagable with the coupling element, the compression nut adapted to rotatingly move downward into the coupling element to translate a force to the top saddle to compress the stabilizer rod between the top saddle and the bottom saddle, wherein the top saddle is rotatingly attached to the compression nut such that the top saddle self-aligns into a secure engagement with the stabilizer rod as the top saddle moves downward toward the stabilizer rod.

In another aspect, there is disclosed a bone stabilizer assembly, comprising a fixation element adapted to engage a bone; a coupling element adapted to couple to the fixation element and to a stabilizer rod; a bottom saddle movably attached to the coupling element and having a first contact surface for contacting a bottom of the stabilizer rod when the stabilizer rod is coupled to the coupling element; a compression element adapted to be rotatingly coupled to the coupling element for transmitting a compression force against the stabilizer rod when the stabilizer rod is coupled to the coupling element; and a top saddle rotatingly attached to the compression element, wherein the top saddle is positioned between the compression element and the stabilizer rod when the stabilizer rod and the compression element are coupled to the coupling element.

In another aspect, there is disclosed a bone stabilizer assembly, comprising a fixation element having a head portion and a shank portion; a coupling element having (1) an internal bore for receiving the shank portion of the fixation element; (2) a seat for receiving the head portion of the fixation element, and (3) a pair of opposed projections having internal threads; a compression nut having external threads engagable with the internal threads of the coupling element such that the compression nut can be rotated downwardly into the coupling element; a top saddle rotatingly attached to a bottom of the compression nut for engaging a top region of a stabilizer rod; and a bottom saddle positioned in the coupling element above the seat for engaging a bottom region of the stabilizer rod, wherein the compression nut provides a downward compression force that compresses the stabilizer rod between the top and bottom saddle when the stabilizer rod is positioned in the coupling element.

The details of one or more embodiments are set forth in the accompanying drawings and the description below. Other features, objects, and advantages will be apparent from the description and drawings, and from the claims.

DETAILED DESCRIPTION

Disclosed are spinal fusion assemblies for use in skeletal systems. The assemblies may be used in any skeletal region, although they are well adapted for the fixation and manipulation of the spine. In a poly-axial embodiment, the system includes a tulip-like coupling element that can be coupled to a fixation element, such as, for example, a screw with a head that removably mates with the coupling element. The coupling element and fixation element are configured to be coupled to an elongate stabilizer, such as a rod, that is positioned between a top and a bottom saddle. A compression member, such as a compression nut, is configured to mate with the coupling element and provides a compressive force to the top and bottom saddles to secure the elongate stabilizer therebetween. The top and bottom saddles are movably positioned within the coupling element such that they can gradually reposition into a secure engagement with the stabilizer as the compression member provides the compressive force.

Figure 1:
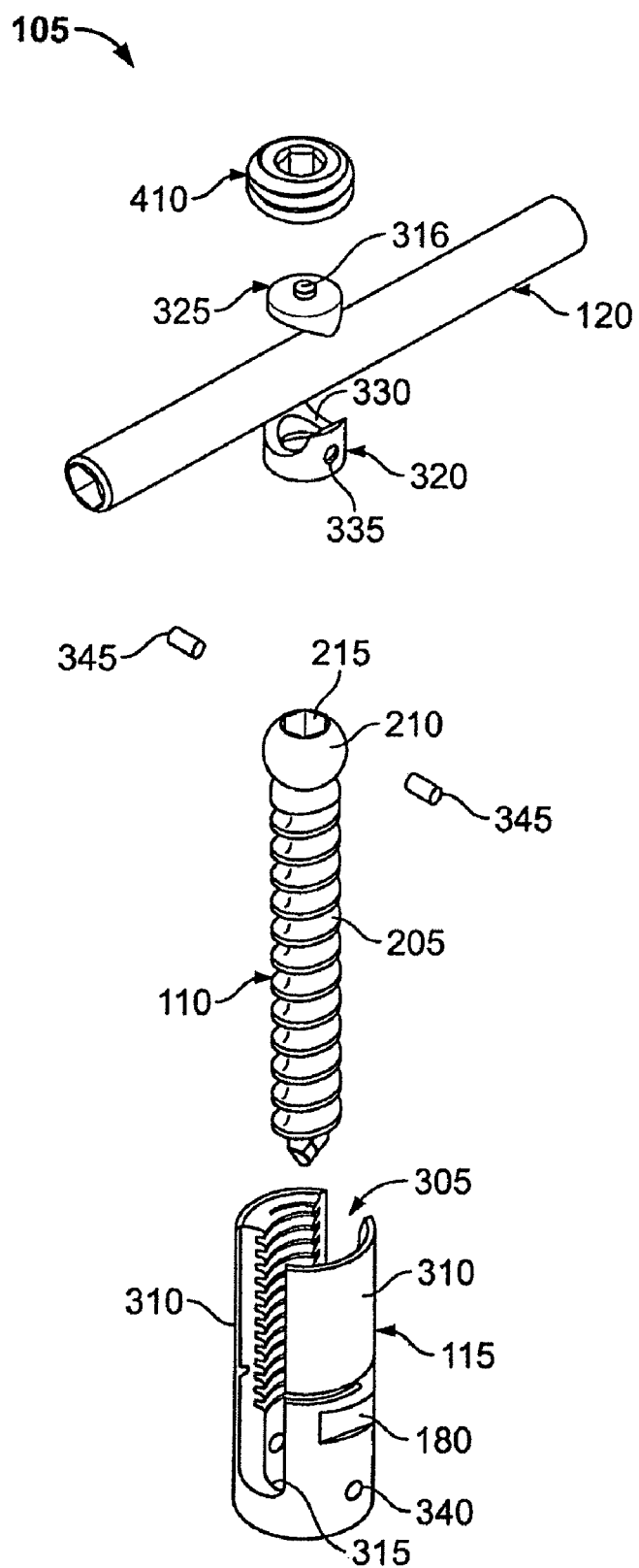
FIG. 1 shows an exploded, perspective view of bone fixation system.
Figures 2, 3:
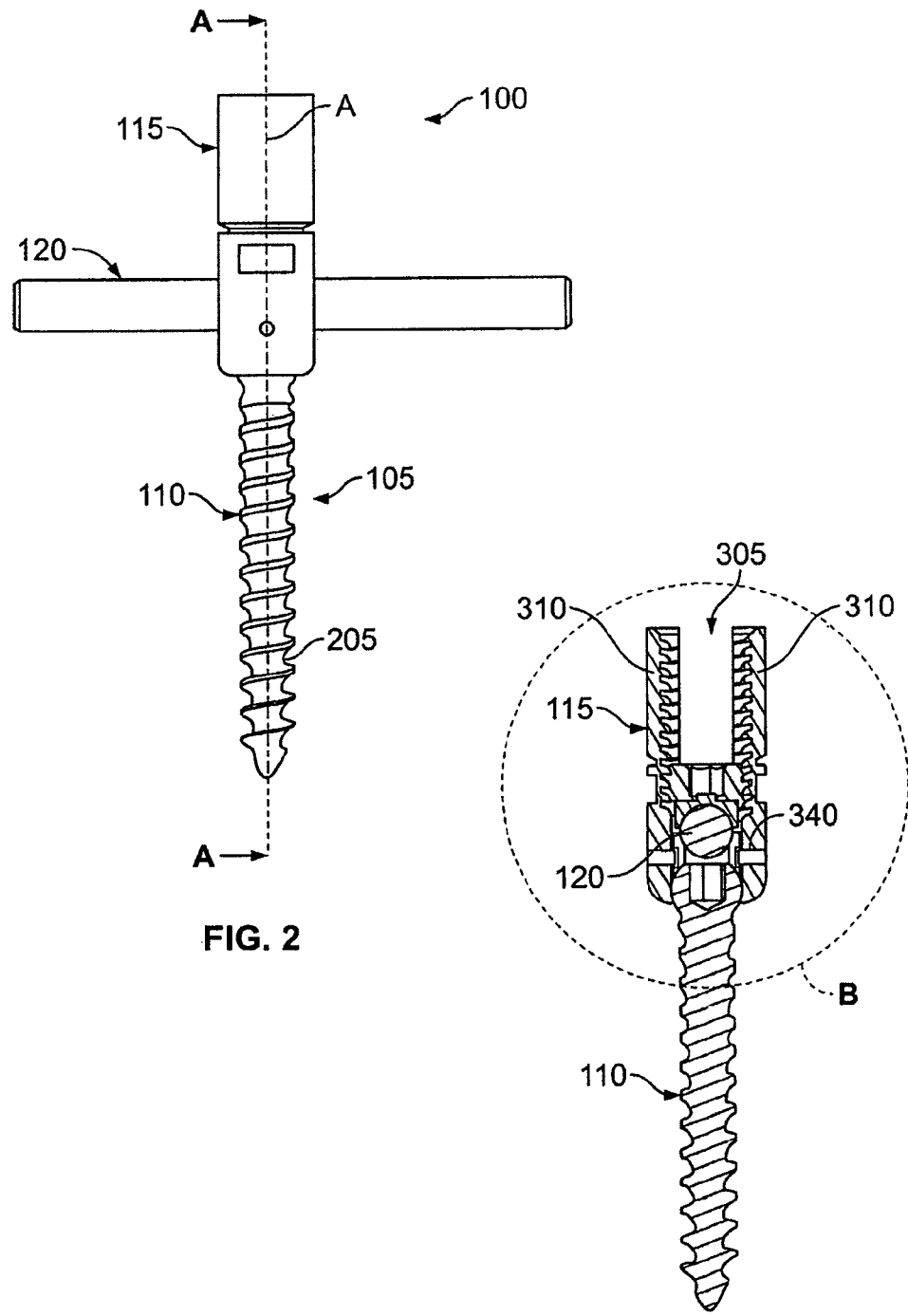
FIG. 2 shows a first side view of the bone fixation system.
FIG. 3 shows a cross-sectional view of the bone fixation system along line A-A of FIG. 2.

FIGS. 1-4 show various views of a polyaxial spinal fusion assembly which is used for the fixation and manipulation of the spine. FIG. 1 shows an exploded view of the polyaxial spinal fusion assembly. FIG. 2 shows a side view of the assembly in an assembled state. With reference to FIGS. 1 and 2, the assembly includes an anchor 105 comprised of a fixation element 110 that is removably coupled to a coupling element 115. The assembly further includes a stabilizer, such as an elongate rod 120, that can be compressively secured to the anchor 105, as described below. FIG. 3 shows a side, cross-sectional view of the assembly 100. As described in detail below, the fixation element 110 can be coupled to a skeletal structure, such as a spinal vertebra. The coupling element 115 is used to couple the fixation element 110 to the stabilizer, which can be coupled to multiple fixation elements using additional couplers.

With reference to FIG. 1, the fixation element 110 can comprise, for example, an elongate screw having a threaded shank portion 205 with external threads that can be screwed into a bone structure such as a vertebra. A head 210 is positioned at the upper end of the shank portion 205. The head 210 has a shape, such as a rounded shape, that is configured to mate with a correspondingly-shaped seat structure in the coupling element 115, as described below. A drive coupler, such as a drive cavity 215 is located within or on the head 210 of the fixation element 110. The drive cavity 215 has a shape that is configured to receive a device that can impart rotational movement to the fixation element 110 in order to screw the fixation element into a bone structure. For example, the drive cavity 215 can have a hexagonal shape that is configured to receive therein an allen-style wrench.

It should be appreciated that the drive coupler need not be a cavity that mates with an allen-style wrench and that other types of drive couplers can be used. Moreover, the fixation element can be in forms other than a shank, including, for example, a hook or clamp. Indeed, it should be appreciated that any structure or component configured for attachment to a bone structure can be used in place of the shank portion of the fixation element.

With reference to FIGS. 1 and 3, the coupling element 115 is configured to receive the fixation element 110 and the elongate rod 120. The coupling element 115 has an internal bore 305 that extends through the coupling element 115 along an axis A (the axis A is shown in FIG. 2). The internal bore 305 is sized to receive at least the shank portion 205 of the fixation element therethrough. A pair of laterally-opposed, upwardly extending projections 310 are separated by the bore 305. The projections 310 have internal, threaded surfaces. In addition, a pair of u-shaped channels 315 extend through the coupling element for receiving therein the rod 120, which extends along an axis that is transverse to the axis A of the bore 350.

The upper ends of the projections 310 define an entry port that is sized to receive therein a compression nut 410 (shown in FIGS. 1 and 4), as described below. The compression nut 410 is described herein as having outer threads that are configured to mate with the inner threads 313 on the opposed inner surfaces of the projections 310 of the coupling element 115. As described below, the entry port is sized and shaped to facilitate an easy entry of the compression nut 410 into or over the projections 310 of the coupling element.

As shown in FIG. 1, a bottom saddle 320 and a top saddle 325 are configured to be positioned within the coupling element 115. The saddles each define a contact surface 330 (shown in FIG. 4) that having a contour selected to complement a contour of the outer surface of the rod 120. In one embodiment, the contact surfaces 330 have rounded contours that complement the rounded, outer surface of the rod 120. However, the contact surfaces 330 can have any shape or contour that complement the shape and contour of the rod 120.

The complementing shapes and contours between the contact surfaces 330 and rod 120 provide a maximum amount of contact area between the saddles and rod 120. For example, the rod 120 is shown having a rounded or convex outer surface. The contact surfaces 330 of the saddles 320, 325 are correspondingly rounded or concave such that the elongate rod 120 can fit snug between the saddles 320, 325 with the contact surfaces 330 of the saddles 320, 325 providing a wide area of contact with the outer surface of the elongate rod 120. It should be appreciated that the contour and shape of the contact surfaces 330 can be varied to match any contour of the outer surface of the elongate rod 120 or in any manner to maximize the amount of grip between the saddles and the elongate rod.

The bottom saddle 320 has an internal bore that axially aligns with the bore 305 in the coupling element 115 when the bottom saddle 320 is placed in the coupling element 115. Furthermore, the bottom saddle 320 has a rounded outer surface that includes a pair of pin cavities 335 (shown in FIGS. 1 and 4) positioned, for example, on opposed locations on the bottom saddle 320. Each of the cavities 335 aligns with a corresponding pin aperture 340 (shown in FIGS. 1 and 4) that extends through the coupling element 115.

The bottom saddle 320 is secured within the coupling element 115 by positioning the saddle between the projections 310 such that each pin cavity 335 in the bottom saddle 320 aligns with a corresponding pin aperture 340 in the coupling element 115. A pin 345 (shown in FIGS. 1 and 4) is then inserted through each pin aperture 340 such that one end of the pin 345 pokes into a corresponding pin cavity 335. The pin 345 provides an interfering engagement with the pin cavity 335 and the pin aperture 340 to thereby secure the bottom saddle 325 in place relative to the coupling element 115.

The diameters of the pins 345 can be smaller than the diameters of the pin cavities 335 so that there is some play therebetween. Furthermore, the pins 345 can have lengths that extend only partially into the pin cavities 335 to provide some play therebetween. This permits the bottom saddle to "float" in the coupling element such that the position and the orientation of the bottom saddle 320 can be varied slightly. That is, the bottom saddle 320 can be moved slightly upward or downward and from side to side when mounted in the coupling element 115. The bottom saddle 320 can also rotate slightly when mounted in the coupling element 115. Thus, the bottom saddle 320 can movingly adjust into a secure engagement with the elongate rod 120 when compressed against the elongate rod 120 during assembly, as described below.

Figure 4:
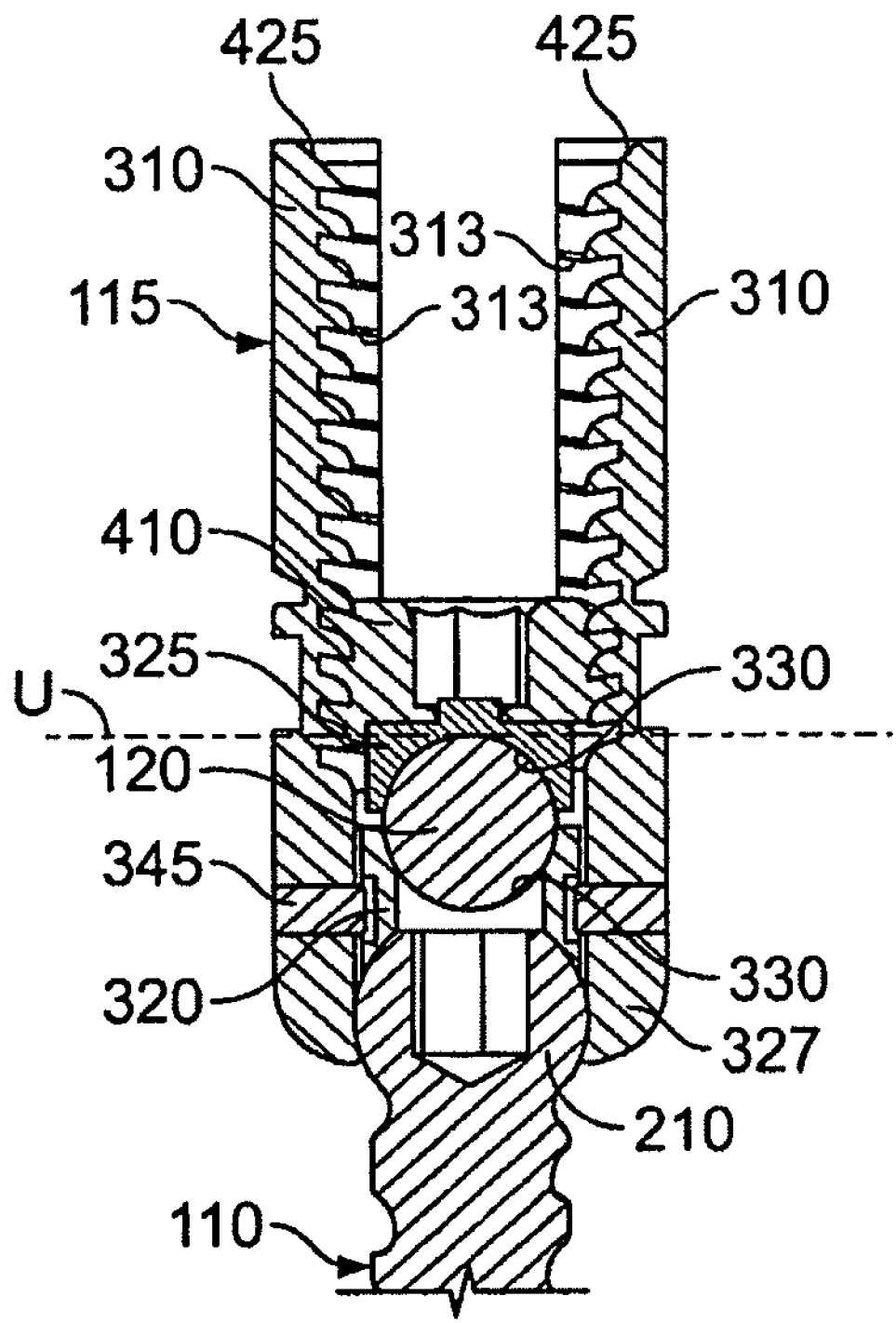
FIG. 4 shows an enlarged view of the region of the bone fixation system contained in circle B of FIG. 3.
Figure 5:
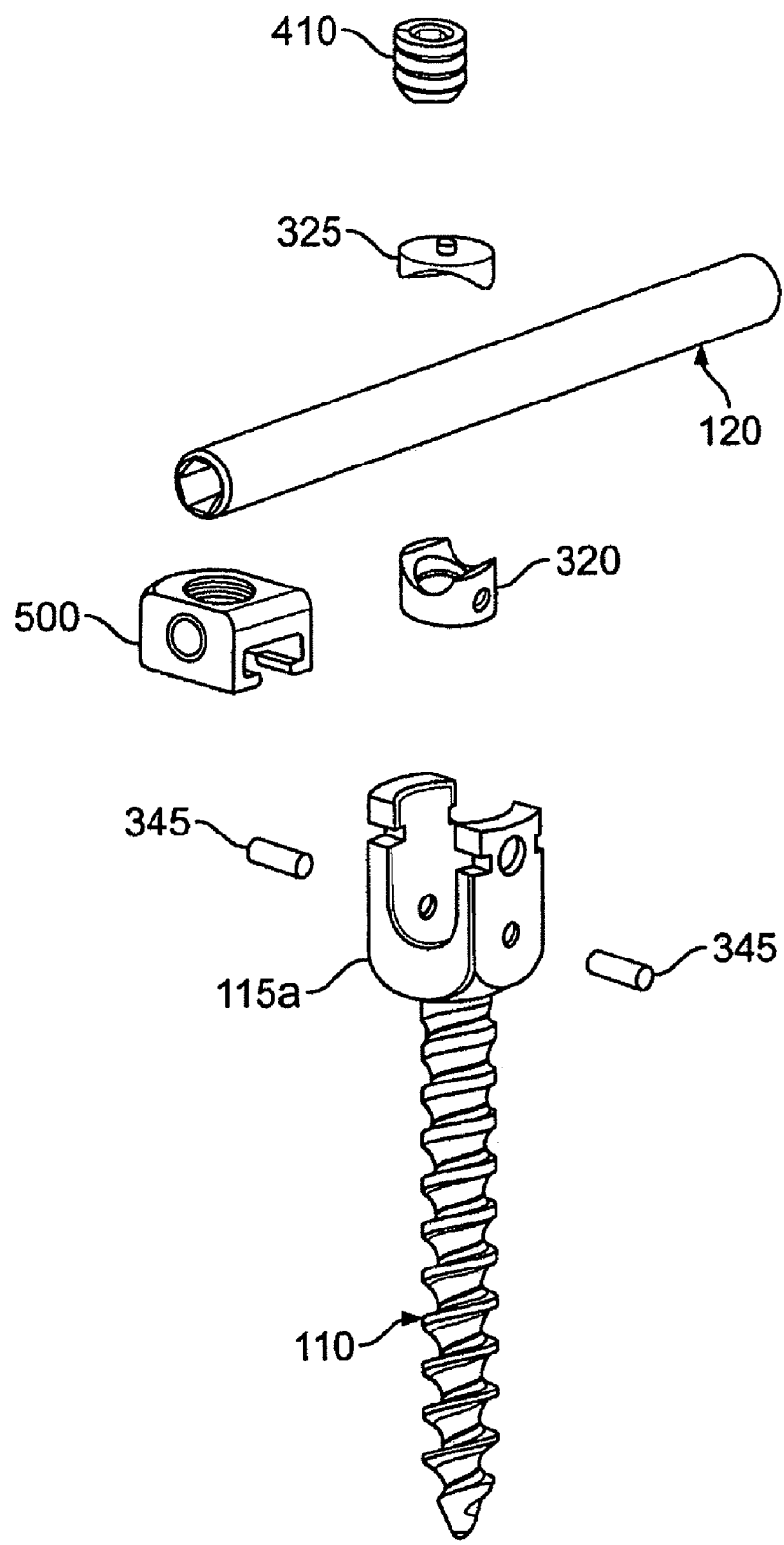
FIG. 5 shows an exploded, perspective view of another embodiment of the bone fixation system.
Figure 6:
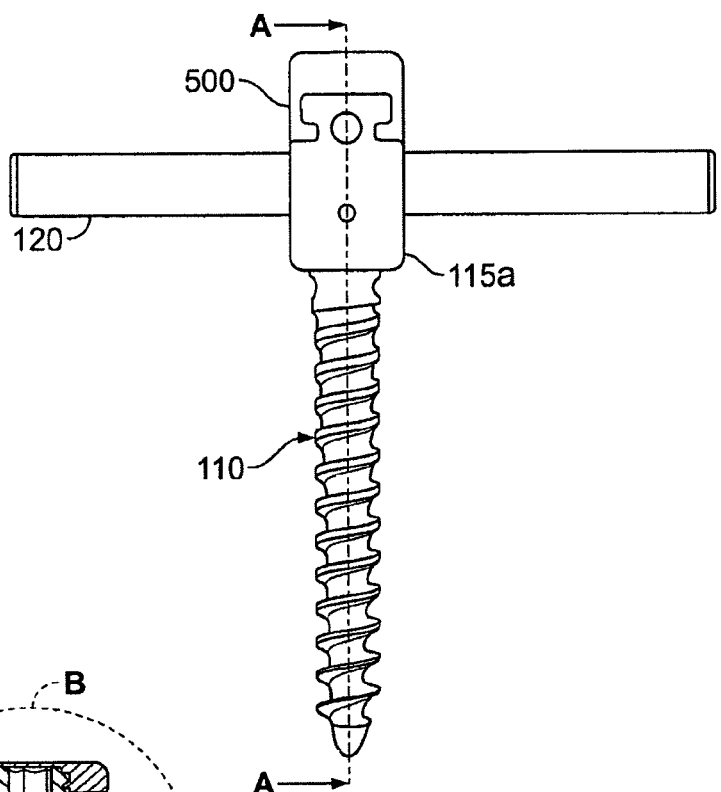
FIG. 6 shows a first side view of the bone fixation system of FIG. 5.
Figure 7:
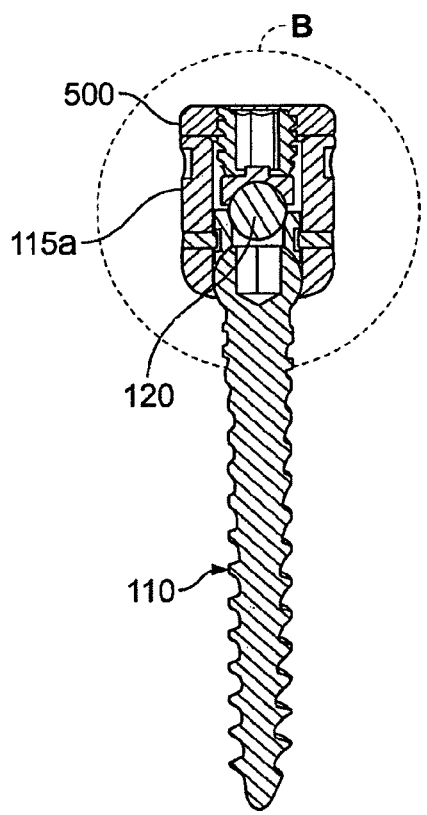
FIG. 7 shows a cross-sectional view of the bone fixation of FIG. 5 system along line A-A of FIG. 5.

With reference to FIGS. 1 and 4, the top saddle 325 is rotatingly mounted within a compression nut 410 that has outer threads that are configured to mate with the threads on the internal surface of the opposed projections 310 of the coupling element 115. In this regard, the top saddle 325 has an upper projection 316 (FIG. 1) that rotatingly mates with the compression nut 410 and permits the top saddle 325 to rotate and/or tilt relative to the compression nut 410 when attached thereto. When attached, the top saddle 325 is positioned immediately below the compression nut 410, as shown in FIG. 4. In another embodiment, the top saddle is fixedly attached to the compression nut 410 such that it does not rotate relative to the compression nut. In another embodiment, there is no top saddle and the compression nut directly contacts the stabilizer rod.

When the compression nut 410 is attached to the top saddle 325, the compression nut 410 is rotatingly coupled to the coupling element 115 by mating the outer threads of the compression nut 410 with the inner threads of the coupling element 115. The compression nut 410 is repeatedly rotated over a 360 degree rotational angle to lower the compression nut into the coupling element. The compression nut 410 is described herein as having outer threads that mate with inner threads on the opposed projections 310. As described below, this advantageously permits a thread configuration that prevents projections 310 from spreading apart from one another as the compression nut 410 is screwed into the coupling element 115. However, it should be appreciated that the compression nut 410 can be modified to have an annular shape with internal threads that mate with corresponding outer threads on the opposed projections 310.

As best shown in FIG. 4, the threads 310 on the inner surfaces of the projections 310 of the coupling element 115 are tilted inwardly with respect to a horizontal axis (a horizontal axis is perpendicular to the axis A shown in FIG. 2). The threads on the exterior of the compression nut 410 are correspondingly tilted. The tilted thread configuration causes the compression nut 410, when screwed into the coupling element 115, to prevent the projections 310 from spreading apart relative to one another. Rather, the compression nut 410 applies a radially inward (i.e., toward the axis A) force to the projections 310 as the compression nut 410 is screwed into the coupling element 115. This keeps the projections 410 from spreading apart while the compression nut 410 is screwed into the coupling element 115.

In addition, the threads are buttressed such that it requires less force to lower or tighten the compression nut 410 into the coupling element 115 and greater force to untighten or loosen the compression nut 410 relative to the coupling element 115. In this manner, it is unlikely that the compression nut will inadvertently loosen from the coupling element over time. This is advantageous, as the assembly can often be mounted in a vertebra for an extended period of time (such as several years) and it is undesirable for the compression nut to inadvertently loosen from the coupling element.

In one embodiment, the various components of the assembly 100 are manufactured of an inert material, such as, for example, stainless steel or titanium.

During assembly of the device, the shank portion 205 of the fixation element 110 is inserted through the bore 305 in the coupling element 115. The rounded head 210 abuts against and sits within a correspondingly-shaped seat 327 in the bottom of the coupling element 115 in a ball/socket manner, as shown in the cross-sectional view of FIG. 4. The seat 327 can have a rounded shape that is configured to provide a secure fit between the head 210 and the coupling element 115. Because the seat 327 is rounded, the head 210 can be rotated within the seat 326 to move the axis of the shank portion 205 to a desired orientation relative to the coupling element 115 and thereby provide a poly-axial configuration.

With the fixation element 110 seated in the coupling element 115, an operator can position the assembly relative to a bone structure such as a vertebra. When the device is fully assembled, the operator can couple a drive device (such as an alien wrench) to the drive cavity 215 in the head 210 and rotate the fixation element 110 to drive the shank portion 205 into a vertebra or other bone structure. As mentioned, the bottom saddle 320 has an internal bore that is sized to receive therethrough the drive device to provide access to the head 210 of the fixation element 110.

With the fixation element 110 positioned in the coupling element 115, the bottom saddle 320 is attached to the coupling element using the pins 340, which mate with the pin cavities 335 in the side of the bottom saddle 320. As discussed, there is some play between the pins 340 and the pin cavities 335, such that the bottom saddle 320 essentially floats and can move somewhat relative to the coupling element 115. That is, the bottom saddle 320 is attached to the coupling element 115 in a manner that permits movement of the bottom saddle 320 relative to the coupling element 115 and/or relative to the elongate rod 120. Thus, the bottom saddle 320 adjusts in position as the compression nut is tightened downward into the coupling element 115, as described below.

The rod 120 is loaded into the coupling element 115 by inserting the rod downwardly between the projections 310 through the u-shaped channels 315, as shown in FIG. 2. As the rod 120 is moved downwardly into the coupling element 115, the outer surface of the rod 120 will eventually abut and sit against the corresponding rounded contact surface 330 of the bottom saddle 320. The compression nut 410 and attached upper saddle 325 are then threaded downward into the coupling element 115 by mating the external threads on the compression nut 410 with the internal threads on the projections 310 of the coupling element 115. The compression nut 410 can be threaded downward until the rod 120 is compressed between the top and bottom saddles, with the compression nut 410 providing the compression force.

As mentioned, the coupling element 115 has an entry port for the compression nut 410 that facilitates entry or coupling of the compression nut 410 into the coupling element 115. The entry port is defined by the upper edges of the projections 310. The entry port has a structure that guides the compression nut into a proper engagement with the coupling element 115. For example, one or more large chamfers 425 (shown in FIG. 4) are located on the upper, inner edge of the projections 310 of the coupling element 115 to provide ease of entry for the compression nut 410 into the coupling element 115. In one embodiment, the chamfers 425 are angled with the angle being in the range of thirty degrees to sixty degrees relative to vertical axis A, although the angle can vary. The chamfers 425 guide the compression nut 410 into proper alignment with the coupling element 115 such that the threads on the compression nut properly engage the threads on the opposed projections 310 without any cross-threading.

The compression nut 410 is then threaded downwardly by repeatedly rotating the compression nut 410 about a 360 degree rotation. As the compression nut 410 lowers into the coupling element, the rounded contact surface 330 of the top saddle 325 abuts the rod 120 and compresses the rod 120 against the rounded contact surface 330 of the bottom saddle 320, as shown in FIG. 4. As mentioned the bottom saddle 320 has a floating arrangement with the coupling element 115 and the top saddle 325 is movable and rotatable relative to the compression nut 410. This permits the saddles to gradually reposition themselves into a secure purchase with the rod 120 as the compression nut 410 moves downward. The contact surfaces 330 of the saddles provide a continuous and maximized area of contact between the saddles and the rod 120 for a secure and tight fit therebetween.

Figure 15:
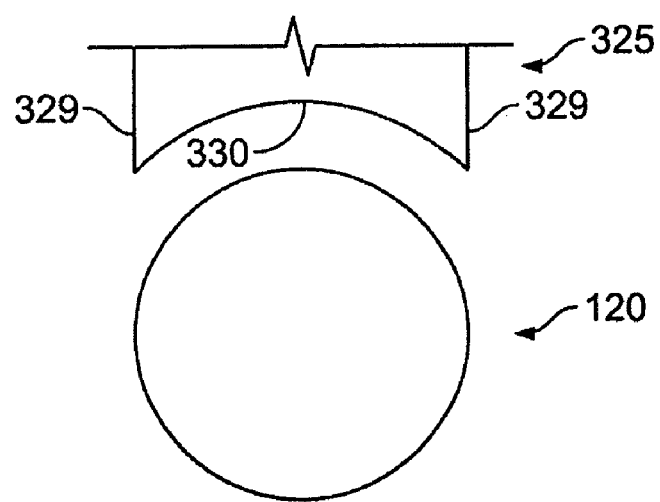
FIG. 15 shows a schematic side view of a top saddle component of the bone fixation system.

Moreover, as shown in FIG. 15, the top saddle 325 is shaped so that opposed wings or protrusions 329 are located on opposed sides of the top saddle 325. The opposed protrusions 329 are positioned on either side of the rod 120 so as to automatically guide the saddle 325 into alignment with the rod 120 as the saddle 325 lowers onto the rod. Because the top saddle 325 can freely rotate as the compression nut lowers onto the rod 120, the protrusions 329 will abut opposed sides of the rod 120 as the top saddle 325 is lowered into the coupling element 115. The top saddle 325 thus self-aligns into a secure engagement with the rod 120 as the top saddle 325 is lowered onto the rod 120.

In one embodiment, the protrusions 329 of the top saddle are formed by a concave contour of the top saddle contact surface 330. It should be appreciated that the protrusions 329 need not be formed from curved surfaces, but can also be formed from straight surfaces. Moreover, the protrusions 329 need not be formed from a continuous, elongated surface, but can rather comprise one or more discrete protrusions, such as spikes, that extend downwardly from the top saddle 325.

As the compression nut 410 is threaded downward, the downward force of the compression nut 410 is transferred to the bottom saddle 320 via the top saddle 325 and the rod 120. This causes the bottom saddle 320 to also moved downward so as to press downward against the head 210 of the fixation element 110. The head 210 is thereby pressed downward into the seat 327 in a fixed orientation. In this manner, the position of the fixation element 110 relative to the coupling element 115 is fixed. That is, the head 210 of the fixation element 210 is pressed downward into the seat of the coupling element with a force sufficient to lock the position of the head 210 relative to the coupling element.

The compression nut 410 can be tightened to provide a sufficient downward force that locks the positions of the saddles relative to the coupling element and the elongate rod. The compression nut 410 thereby provides a downward force that locks the relative positions of the elongate rod, saddles, coupling element, and fixation element 110. After this is complete, the upper portion of the opposed projections 310 of the coupling element can be snapped off at a predetermined location along the length of the projections 310.

As discussed, inner threads 313 are located on the opposed inner faces of the projections 310. The threads 313 extend downwardly along the projections 310 to a depth that is sufficient to provide secure engagement between the threads on the projections 313 and the threads on the compression nut 410 when the compression nut is fully tightened. It should be appreciated that the threads 313 do not have to extend to a depth below the upper surface (identified by line U in FIG. 4) of the rod 120 when the rod 120 is positioned in the coupling element 115. In one embodiment, the threads 313 extend to a depth that is above the upper surface (identified by line U) of the rod 120. The top saddle 325 provides a spacing between the rod 120 and the compression nut 410, which permits such thread depth.

FIGS. 5-8 show another embodiment of a polyaxial spinal fusion assembly. Unless noted otherwise, the descriptions of elements of the foregoing embodiment apply to the descriptions of the elements of the embodiment of FIGS. 5-8. In FIGS. 5-8, like numerals refer to like parts with respect to the device of FIGS. 1-4. In this embodiment, the coupling element 115a has a head region that slidingly mates with a cap 500 having a threaded, internal bore that co-axially aligns with the internal bore 305 in the coupling element 115a.

Figure 8:
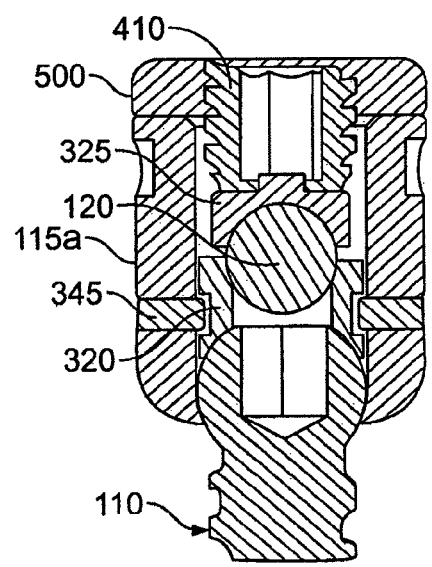
FIG. 8 shows an enlarged view of the region of the bone fixation system contained in circle B of FIG. 7.

As shown in FIG. 5-8, the cap 500 has a pair of downwardly-extending arms having a shape that slidingly mates with correspondingly-shaped cavities in the head of the coupling element. The cap 500 slides into engagement with the head of the coupling element along an axis that is transverse to the axis of the shank portion 205 of the fastening element 110. As shown in FIG. 8, outer threads on the compression nut 410 engage internal threads on the cap 500 to secure the compression nut therein. The rod 120 can then be secured between the upper saddle 325 and lower saddle 320 in the manner described above.

Figure 9:
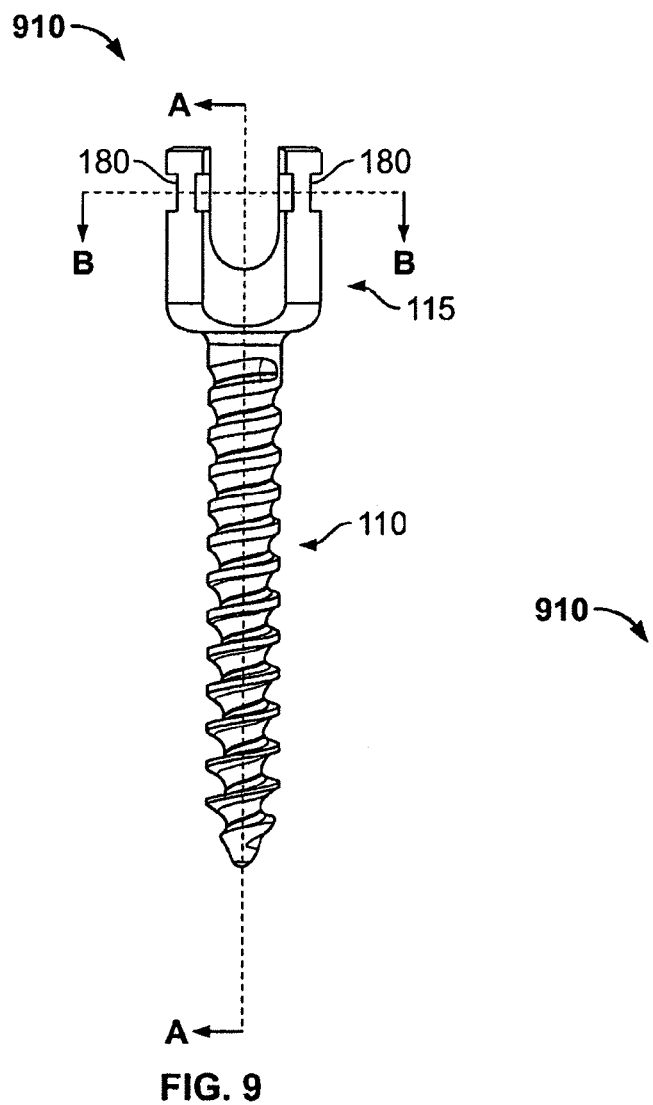
FIG. 9 shows a side view of a mono-axial bone fixation system.

FIG. 9 shows another embodiment of a spinal fusion assembly comprising a mono-axial anchor 910. The anchor 910 comprises a fixation element 110 that is integrally attached to a coupling element 115. Unlike the poly-axial embodiment, the coupling element 115 in the mono-axial anchor 910 is not removably coupled to the fixation element 110. This provides the fixation element 110 with a fixed axis relative to the coupling element 115 and the elongate rod to which the coupling element 115 is coupled.

Figure 10:
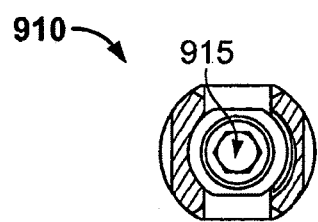
FIG. 10 shows a cross-sectional view of the system of FIG. 9 along line B-B of FIG. 9.
Figure 11:
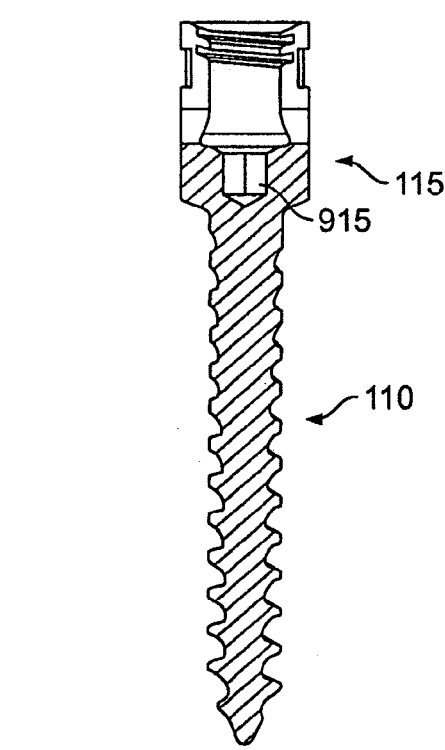
FIG. 11 shows a cross-sectional view of the system of FIG. 9 along line A-A of FIG. 9.

FIG. 10 shows a cross-sectional view of the anchor 910 along line B-B of FIG. 9 and FIG. 11 shows a cross-sectional view along line A-A of FIG. 9. A driver coupler comprised of a cavity 915 is disposed in an upper region of the anchor 910 above the fixation element 110. The cavity 915 has a shape that is configured to mate with a drive tool, such as a wrench or a screwdriver, for driving the fixation element 110 into a bone structure. In one embodiment, the cavity is hexagonal-shaped and is the same shape as the drive cavity (FIG. 1) in the poly-axial anchor 105. A hexagonal shape provides a secure engagement between the cavity 915 and the drive tool. Furthermore, where the cavity 915 is the same size and shape as the drive cavity 215 in the poly-axial embodiment, a surgeon can use a single, universal tool for both the mono-axial and poly-axial anchors.

Figure 12:
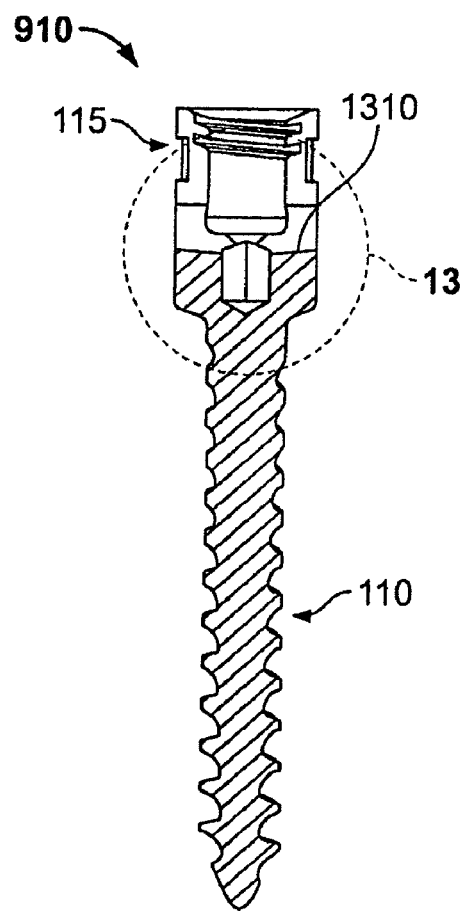
FIG. 12 shows another side view of a mono-axial bone fixation system.
Figure 13:
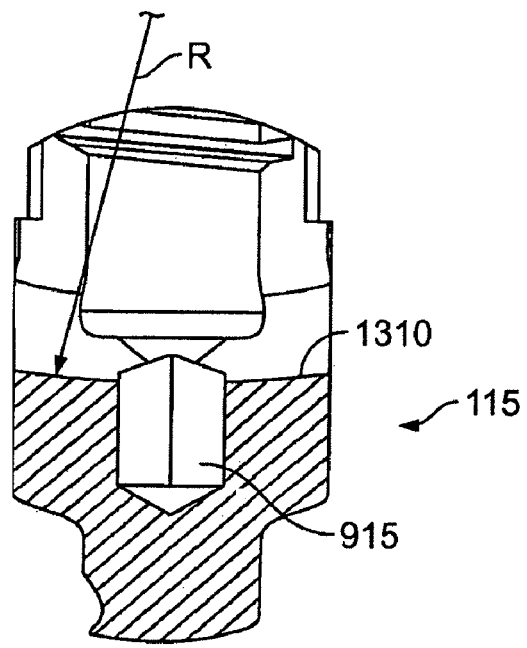
FIG. 13 shows an enlarged view of the region of the bone fixation system contained in circle 13 of FIG. 12.

With reference to FIGS. 12 and 13, the coupling element 115 of the anchor 910 has a rod contact surface 1310 that is sized and shaped to support and interface with an elongate rod. As best shown in the enlarged view of FIG. 13, the rod contact surface 1310 has a radius of curvature R to provide the rod contact surface with a concave shape.

Figure 14:
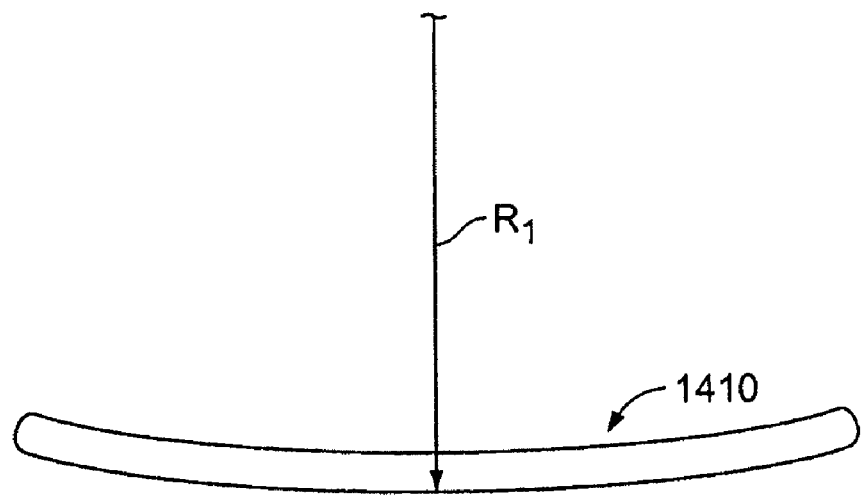
FIG. 14 shows a side view of a stabilizer rod configured to couple to the bone fixation system of FIG. 12.

FIG. 14 shows a side-view of a rod 1410 that couples to the coupling element 115 of the anchor 910. Like the rod contact surface 1310, the rod 1410 also has a radius of curvature, R1. The radius of curvature R1 of the rod 1410 is equal to or substantially equal to the radius of curvature R of the rod contact surface 1310 of the anchor 910. Accordingly, when the rod 1410 is positioned on the rod contact surface 1310, the common radius of curvature provides a smooth and large contact area between the rod 1410 and the rod contact surface 1310. This provides a secure attachment between the rod 1410 and the anchor 910.

With reference to FIGS. 1 and 9, both the poly-axial and mono-axial embodiments can include one or more tool-connection surfaces 180 that can be interfaced with a tool for grasping or rotating the anchor. The tool connection surfaces 180 are desirably positioned on the outer surfaces of the coupling element 115 as the coupling element 115 is typically the location where a surgeon holds the anchor. However, it should be appreciated that the tool connection surfaces can be disposed on other locations on the anchors. The tool connection surfaces 180 comprise a cut-out or flattened region of the coupling element 115. In one embodiment, the tool connection surfaces 180 are inclined, flat surfaces that are disposed on the rounded, outer surfaces of the coupling element 115.

The tool connection surface 180 provides a location where one or more tools, such as wrenches or pliers, can securely interface with the anchor. The tool connection surfaces can be flat or they can have a contour or shape that is selected to specifically correspond to the shape of a grasping element of the tool. Several tool connection surfaces 180 can be positioned on the anchor and can be inclined at various angles relative to provide various locations and orientations for grasping by a tool.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

What is claimed:

1. A bone stabilizer assembly, comprising:
a fixation element configured to engage a bone and having a head portion and shank portion;
a coupling element having an internal bore sized to receive the shank portion of the fixation element and a seat adapted to support the head portion of the fixation element, the coupling element further adapted to receive a stabilizer rod;
a compression nut configured to be received within the internal bore of the coupling element and be rotated downwardly into the coupling element;
a top saddle rotatingly attached to a bottom of the compression nut via an upwardly extending projection, the top saddle being configured to rotate freely relative to the compression nut to securely engage a top region of the stabilizer rod as the compression nut is rotated downwardly into the coupling element, wherein the top saddle is configured to tilt relative to the compression nut; and
a bottom saddle movably mounted in the coupling element below the stabilizer rod, when the stabilizer rod is in the coupling element, the bottom saddle being securable within the coupling element, such that when the bottom saddle is mounted in the coupling element, the bottom saddle and the coupling element are coupled together and the coupling of the coupling element and the bottom saddle permit limited downward movement of the bottom saddle relative to the coupling element.

2. The bone stabilizer assembly of claim 1, wherein the top saddle is positioned above the stabilizer rod when the stabilizer rod is in the coupling element.

3. The bone stabilizer assembly of claim 1, wherein the compression nut is adapted to rotatingly move downward into the coupling element and to translate a force to the top saddle to compress the stabilizer rod between the top saddle and the bottom saddle.

4. The bone stabilizer assembly of claim 1, wherein the top saddle comprises wings located opposed sides of the top saddle that self-aligns the top saddle into a secure engagement with the stabilizer rod as the top saddle moves downward toward the stabilizer rod.

5. The bone stabilizer assembly of claim 1, further comprising a connector pin connecting the bottom saddle to the coupling element, wherein the connector pin extends at least partially into the bottom saddle such that the bottom saddle can move relative to the coupling element.

6. The bone stabilizer assembly of claim 1, wherein the coupling of the coupling element and the bottom saddle permits the bottom saddle to adjust in position as the compression nut rotatingly moves downward into the coupling element.

7. The bone stabilizer assembly of claim 1, wherein the compression nut is configured to be rotated downwardly into the coupling element by repeatedly rotating the compression nut about a 360-degree rotation.

8. The bone stabilizer assembly of claim 1, wherein the compression nut is configured to be rotated downwardly into the coupling element by mating external threads on the compression nut with internal threads on an internal surface of the coupling element.

9. The bone stabilizer assembly of claim 1, wherein the bottom saddle has a first contact surface configured to engage a bottom surface of the stabilizer rod, and the top saddle has a second contact surface configured to engage the top surface of the stabilizer rod.

10. The bone stabilizer assembly of claim 9, wherein the second contact surface is concave and the top and bottom of the stabilizer rod is convex.

* * * * *

UNITED STATES PATENT AND TRADEMARK OFFICE
CERTIFICATE OF CORRECTION

PATENT NO.         : 8,273,112 B2
APPLICATION NO.    : 12/725401
DATED              : September 25, 2012
INVENTOR(S)        : Laszlo Garamszegi et al.

It is certified that error appears in the above-identified patent and that said Letters Patent is hereby corrected as shown below:

In Column 10, claim 4, line 2, insert --on-- between located and opposed.

Claim 4 should read:

The bone stabilizer assembly of claim 1, wherein the top saddle comprises wings located on opposed sides of the top saddle that self-aligns the top saddle into a secure engagement with the stabilizer rod as the top saddle moves downward towards the stabilizer rod.

Signed and Sealed this
Eighteenth Day of December, 2012

David J. Kappos
*Director of the United States Patent and Trademark Office*

UNITED STATES PATENT AND TRADEMARK OFFICE
CERTIFICATE OF CORRECTION

PATENT NO. : 8,273,112 B2
APPLICATION NO. : 12/725401
DATED : September 25, 2012
INVENTOR(S) : Laszlo Garamszegi et al.

It is certified that error appears in the above-identified patent and that said Letters Patent is hereby corrected as shown below:

Column 10, line 23 (claim 4, line 2) insert --on-- between located and opposed.

Column 10, lines 22-26, Claim 4 should read:

--The bone stabilizer assembly of claim 1, wherein the top saddle comprises wings located on opposed sides of the top saddle that self-aligns the top saddle into a secure engagement with the stabilizer rod as the top saddle moves downward towards the stabilizer rod.--

This certificate supersedes the Certificate of Correction issued December 18, 2012.

Signed and Sealed this
Nineteenth Day of February, 2013

Teresa Stanek Rea
*Acting Director of the United States Patent and Trademark Office*

(12) EX PARTE REEXAMINATION CERTIFICATE (9751st)
United States Patent
Garamszegl et al.

(10) Number: US 8,273,112 C1
(45) Certificate Issued: Jul. 16, 2013

(54) PEDICLE SCREW ASSEMBLY

(75) Inventors: Laszlo Garamszegl, Mission Viejo, CA (US); John Carlisle Brown, Balboa, CA (US); Souhail Toubia, San Juan Capistrano, CA (US)

(73) Assignee: Phygen, LLC, Irvine, CA (US)

Reexamination Request:
No. 90/012,701, Oct. 11, 2012

Reexamination Certificate for:
Patent No.: 8,273,112
Issued: Sep. 25, 2012
Appl. No.: 12/725,401
Filed: Mar. 16, 2010

Certificate of Correction issued Dec. 18, 2012
Certificate of Correction issued Feb. 19, 2013

Related U.S. Application Data

(63) Continuation of application No. 11/109,124, filed on Apr. 18, 2005, now Pat. No. 7,678,139.

(60) Provisional application No. 60/563,594, filed on Apr. 20, 2004, provisional application No. 60/598,676, filed on Aug. 3, 2004, provisional application No. 60/612,885, filed on Sep. 24, 2004.

(51) Int. Cl.
*A61B 17/86* (2006.01)

(52) U.S. Cl.
USPC .......... 606/306; 606/266; 606/267; 606/270; 606/305; 606/328

(58) Field of Classification Search
None
See application file for complete search history.

(56) References Cited

To view the complete listing of prior art documents cited during the proceeding for Reexamination Control Number 90/012,701, please refer to the USPTO's public Patent Application Information Retrieval (PAIR) system under the Display References tab.

*Primary Examiner* — Jeanne M Clark

(57) ABSTRACT

Disclosed are spinal fusion assemblies for use in skeletal systems. The assembly includes a coupling element that can be coupled to a fixation element, such as, for example, a screw with a head that removably mates with the coupling element. The coupling element and fixation element are configured to be coupled to an elongate stabilizer, such as a rod, that is positioned between a top and a bottom saddle. A compression member, such as a compression nut, is configured to mate with the coupling element and provides a compressive force to the top and bottom saddles to secure the elongate stabilizer therebetween. The top and bottom saddles are movably positioned within the coupling element such that they can gradually reposition and self-align into a secure engagement with the stabilizer as the compression member provides the compressive force.

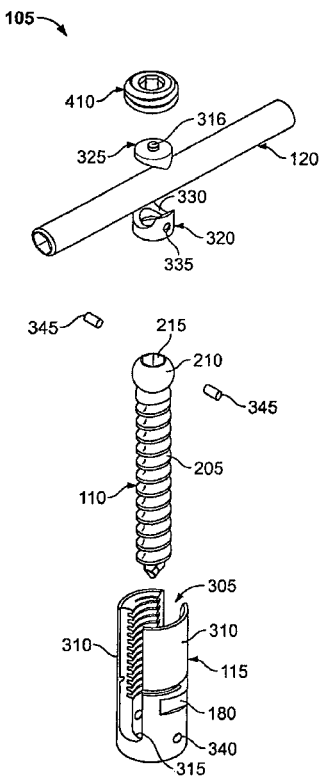

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-10 are cancelled.

\* \* \* \* \*